(12) United States Patent
Ushijima

(10) Patent No.: US 8,740,776 B2
(45) Date of Patent: Jun. 3, 2014

(54) ENDOSCOPIC FLUID CONTROL APPARATUS

(75) Inventor: Takanori Ushijima, Tama (JP)

(73) Assignee: Olympus Medical Systems Corp. (JP)

( * ) Notice: Subject to any disclaimer, the term of this patent is extended or adjusted under 35 U.S.C. 154(b) by 454 days.

(21) Appl. No.: 12/883,307

(22) Filed: Sep. 16, 2010

(65) Prior Publication Data

US 2011/0071357 A1    Mar. 24, 2011

Related U.S. Application Data

(63) Continuation of application No. PCT/JP2009/069506, filed on Nov. 17, 2009.

(30) Foreign Application Priority Data

Mar. 30, 2009    (JP) ................................ 2009-082917

(51) Int. Cl.
    *A61B 1/12*    (2006.01)
(52) U.S. Cl.
    USPC ......................................... 600/159; 600/158
(58) Field of Classification Search
    USPC ................................. 600/155–159
    See application file for complete search history.

(56) References Cited

U.S. PATENT DOCUMENTS

| | | | | |
|---|---|---|---|---|
| 4,193,406 A * | 3/1980 | Jinotti | ....................... | 128/204.18 |
| 4,408,598 A * | 10/1983 | Ueda | ............................. | 600/159 |
| 4,852,551 A | 8/1989 | Opie et al. | | |
| 6,383,132 B1 * | 5/2002 | Wimmer | ....................... | 600/159 |
| 6,569,087 B2 * | 5/2003 | Naito et al. | .................... | 600/156 |

FOREIGN PATENT DOCUMENTS

| | | |
|---|---|---|
| JP | 1-120802 | 8/1989 |
| JP | 8-299265 | 11/1996 |
| JP | 9-84756 | 3/1997 |
| JP | 2003-52621 | 2/2003 |
| JP | 2003-199706 | 7/2003 |
| JP | 2004-24561 | 1/2004 |
| JP | 2009-18053 | 1/2009 |
| WO | WO 2007/074442 | 7/2007 |

OTHER PUBLICATIONS

Search Report issued by European Patent Office in connection with corresponding application No. EP 09 84 3069 on Aug. 2, 2011.
English translation of International Search Report issued on Dec. 14, 2009 in connection with corresponding PCT application No. PCT/JP2009/069506.
International Search Report and Written Opinion mailed Dec. 22, 2009 in corresponding PCT International Application No. PCT/JP2009/069506.

* cited by examiner

*Primary Examiner* — Alireza Nia
(74) *Attorney, Agent, or Firm* — Ostrolenk Faber LLP

(57) ABSTRACT

An endoscopic fluid control apparatus is provided in an endoscope including a channel for performing suction and air-feed, and controls the suction and air-feed for the channel. The endoscopic fluid control apparatus includes air-feed channels which communicate with the one channel, a suction channel which communicates with the one channel, a first valve which is provided on the air-feed channels and opens only during the air-feed, and a second valve which is provided on an operation button to be operated for suction operation, and shuts off communication between one of the air-feed channels and another of the air-feed channels among the air-feed channels into which the operation button is inserted, when the operation button is operated to carry out the suction operation.

3 Claims, 14 Drawing Sheets

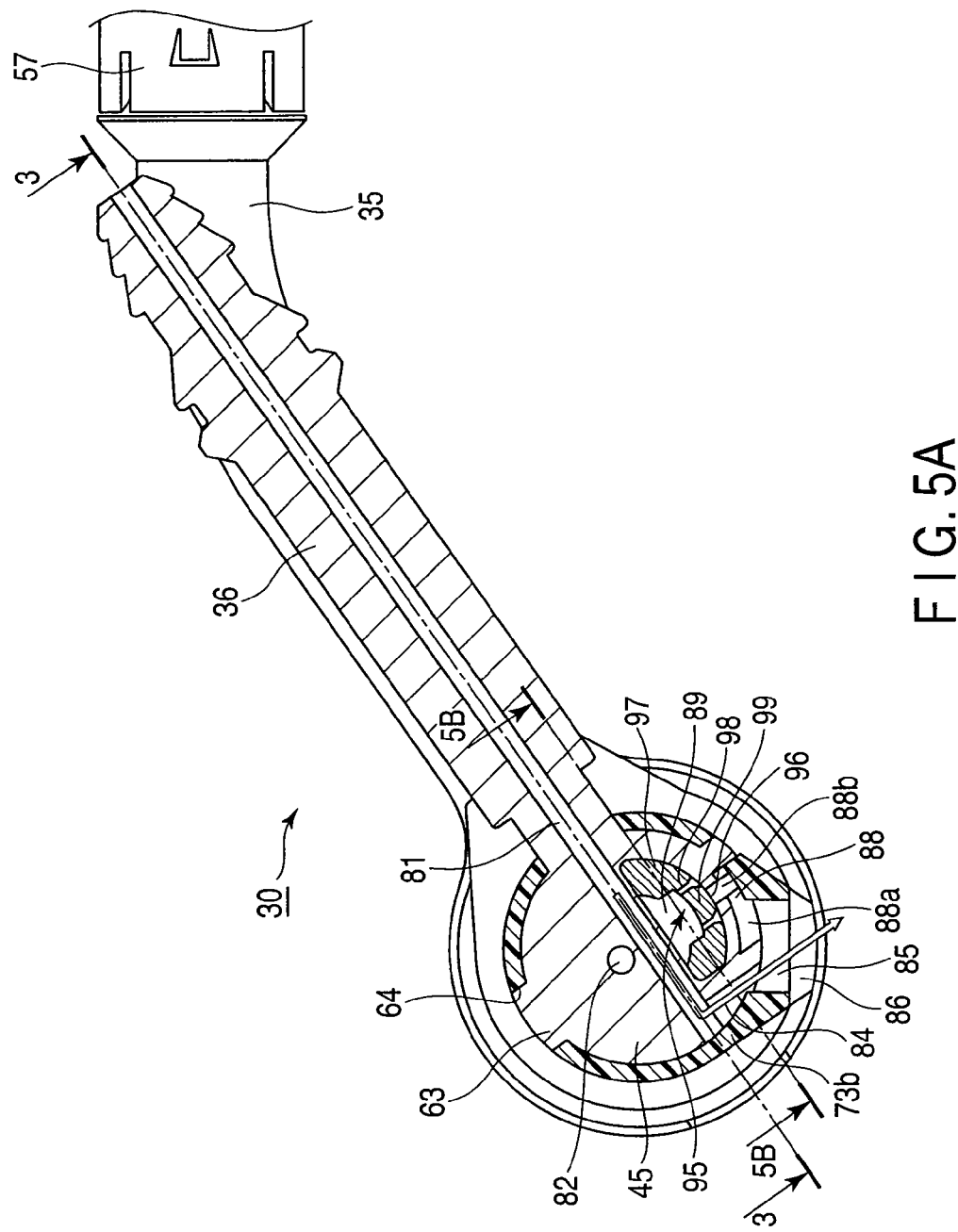
F I G. 5A

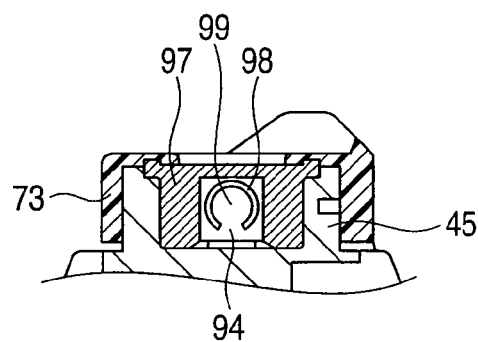
F I G. 5B
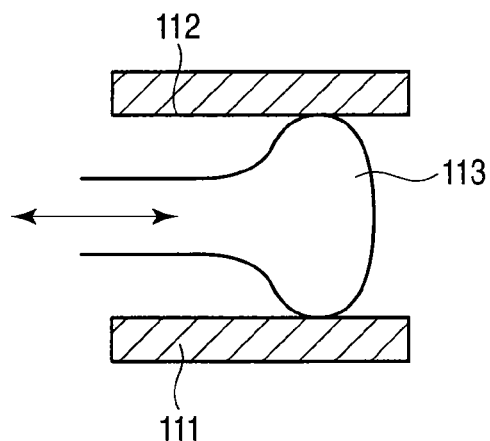
F I G. 6A
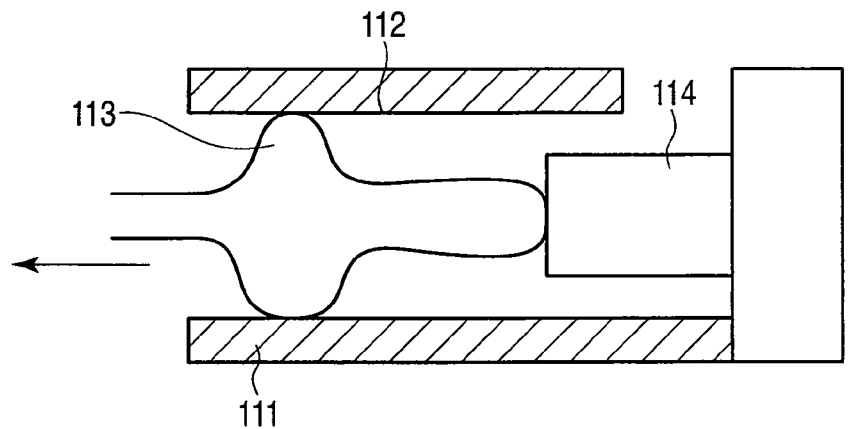
F I G. 6B

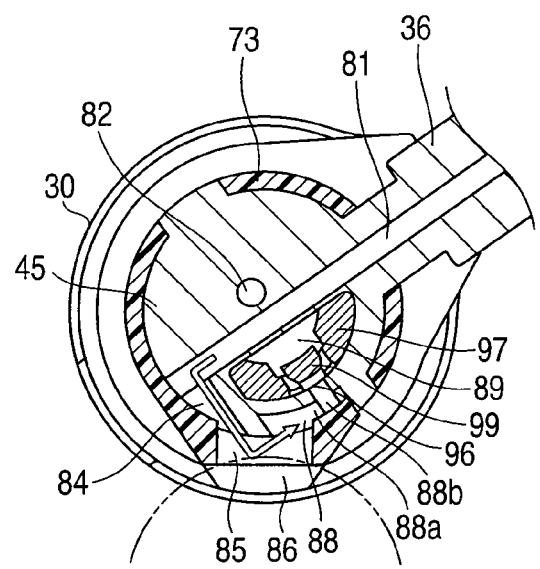
F I G. 7B
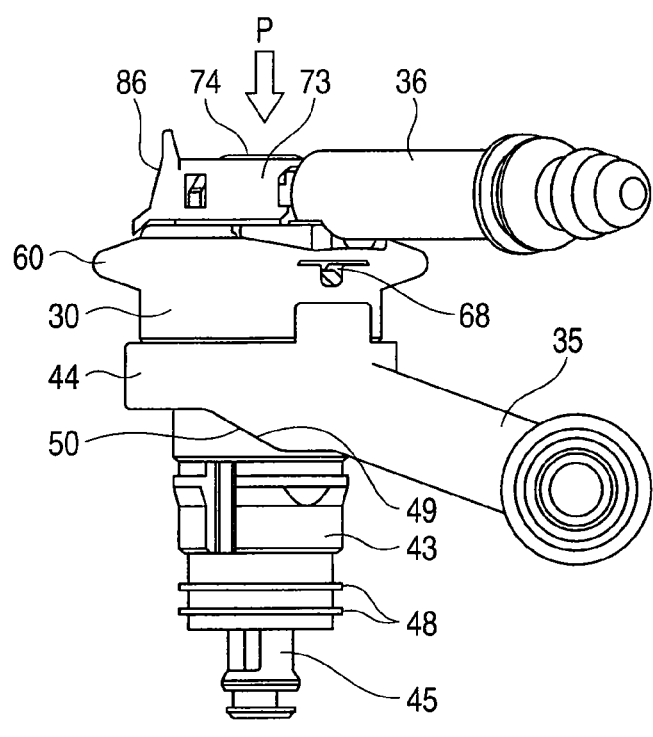
(During suction)
F I G. 8A (During suction)

(During suction)

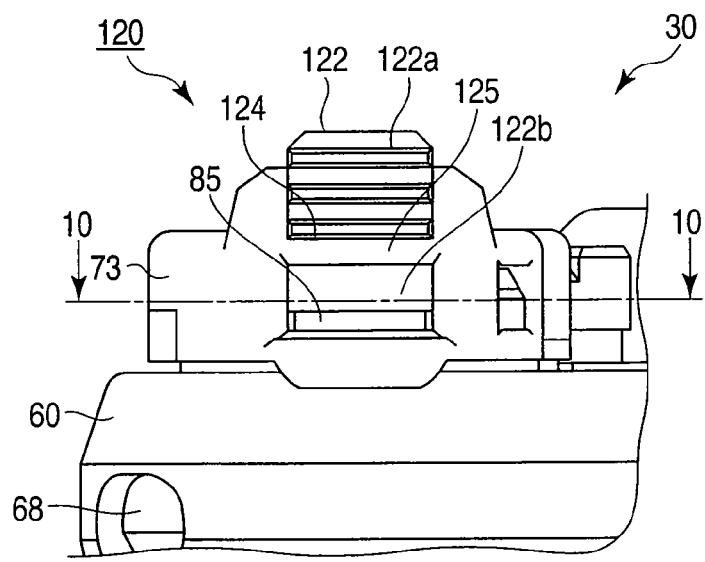
F I G. 9
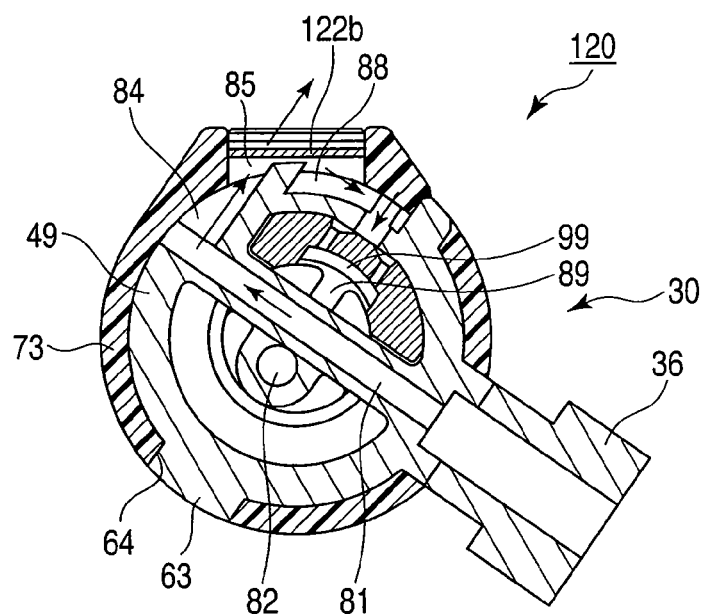
F I G. 10

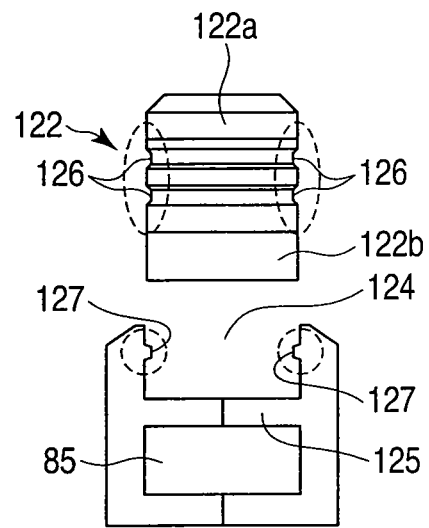
F I G. 13
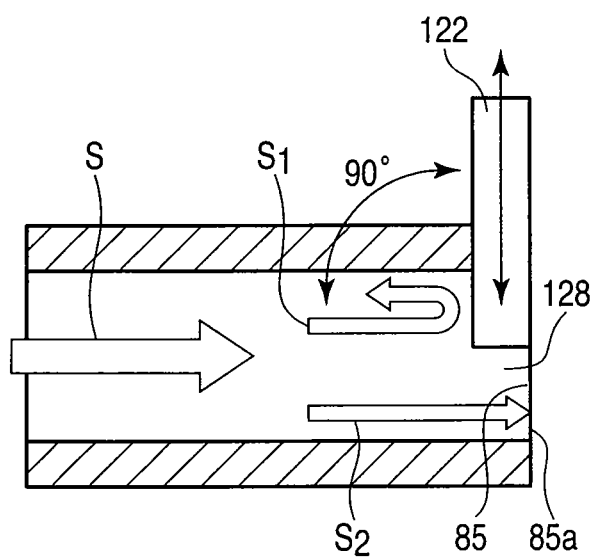
F I G. 14A

ENDOSCOPIC FLUID CONTROL APPARATUS

CROSS REFERENCE TO RELATED APPLICATIONS

This is a Continuation Application of PCT Application No. PCT/JP2009/069506, filed Nov. 17, 2009, which was published under PCT Article 21(2) in Japanese.

This application is based upon and claims the benefit of priority from prior Japanese Patent Application No. 2009-082917, filed Mar. 30, 2009, the entire contents of which are incorporated herein by reference.

BACKGROUND OF THE INVENTION

1. Field of the Invention

The present invention relates to a fluid control apparatus which controls the flow of fluid by performing air feed and suction through one channel in an endoscope.

2. Description of the Related Art

In general, an endoscope comprises an insertion part which is inserted into a body cavity, and a manipulation part connected to a base end of the insertion part. An endoscope also comprises channels through which fluid flows for feeding or suctioning air or water. Movement of fluid is controlled by a fluid control apparatus provided in the manipulation part (see for example, Jpn. Pat. Appln. KOKAI Publication No. 9-84756, Jpn. Pat. Appln. KOKAI Publication No. 2003-52621, and Jpn. Pat. Appln. KOKAI Publication No. 8-299265).

Recently, air feed and suction are performed through one channel in an endoscope. In this case, there has been a proposal for a fluid control apparatus of a method in which a single valve device controls switching between the air feed and suction (see Jpn. Pat. Appln. KOKAI Publication No. 2009-18053).

BRIEF SUMMARY OF THE INVENTION

According to an aspect of embodiments, an endoscopic fluid control apparatus is provided in an endoscope including a channel for performing suction and air feed and controls the suction and air feed for the channel, the apparatus including: air-feed channels which communicate with the one channel; a suction channel which communicates with the one channel; a first valve which is provided on the air-feed channels and opens only during the air-feed; and a second valve which is provided on an operation button to be operated for suction operation, and shuts off communication between one of the air-feed channels and another of the air-feed channels in the air-feed channels into which the operation button is inserted, when the operation button is operated to perform the suction operation.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5A is a cross sectional view illustrating the fluid control apparatus laterally cut along a plane along the center of the metal air-feed mouthpiece (along a line 5A-5A in FIG. 2);

FIG. 5B is a longitudinal sectional view cut along a line 5B-5B in FIG. 5A;

FIG. 6A illustrates a modification of a valve device;

FIG. 6B illustrates a modification of the valve device;

FIG. 7B is a cross sectional view cut along a line 7B-7B in FIG. 7A;

FIG. 8A is a side view of the fluid control apparatus during suction;

FIG. 9 is a front view of a gate device which adjusts a leak rate from an air-feed leak hole of the fluid control apparatus;

FIG. 10 is a cross-sectional view cut along a surface (along a line 10-10 in FIG. 9) penetrating an air-feed leak hole, to illustrate the gate device;

FIG. 13 is a front view illustrating a frame and a gate wall extracted from an air-feed leak hole;

FIG. 14A illustrates an example of providing the gate wall, and a relationship between the gate wall and air-feed flow.

DETAILED DESCRIPTION OF THE INVENTION

Hereinafter, an embodiment of the present invention will be will be described in detail.

Figure 1:
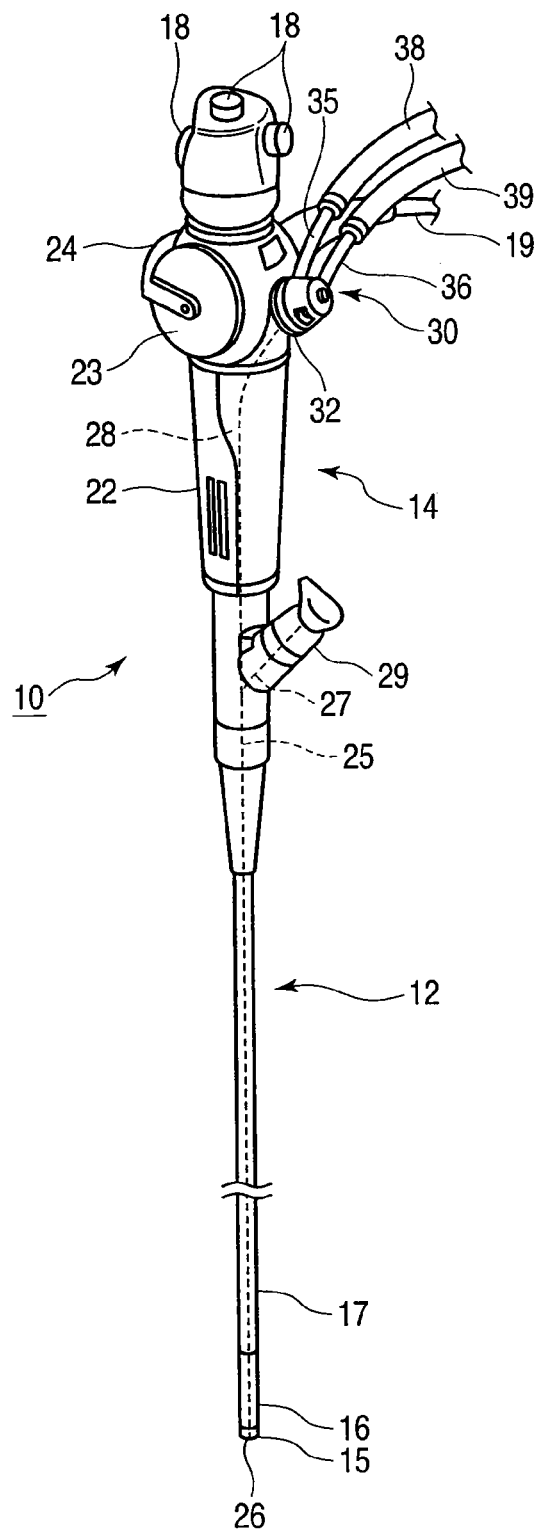
FIG. 1 is a perspective view illustrating an endoscope according to an embodiment of the present invention.

FIG. 1 is a perspective view illustrating an endoscope 10 in an endoscopic device according to an embodiment of the invention. This endoscope 10 comprises an elongate endoscope insertion part 12 which is inserted into a body cavity, and an endoscope manipulation part 14 which is connected to a base end of the endoscope insertion part 12. The endoscope insertion part 12 is constituted by connecting a tip end structure 15, a bendable part 16 which is operated to bend, and a flexible tube part 17 which is long and flexible, in this order from a base end side. An unillustrated illumination window and an imaging observation window are provided in the tip end structure 15. In this manner, the endoscope insertion part 12 is inserted into a body cavity, and the inside of the body cavity is then imaged and observed. The endoscope manipulation part 14 comprises an endoscope grip part 22 which is gripped by an operator, and an endoscope manipulation-part body 23 positioned closer to the base end than the endoscope grip part 22. The endoscope manipulation-part body 23 is provided with a bend lever 24 for bending the bendable part 16. Plural operation switches 18 for controlling imaging are provided at a hand-side part of the endoscope manipulation part 14. A universal cord 19 which guides an unillustrated light guide and a signal cable from a side of the endoscopic device is connected to the endoscope manipulation part 14.

In the endoscope manipulation-part body 23, there is provided a bend drive mechanism (unillustrated) which is operated by the bend lever 24. This bend drive mechanism is operated by the bend lever 24, to bend the bendable part 16 by using an unillustrated manipulation member such as a manipulation wire part inserted in the endoscope insertion part 12.

An insertion channel 25 for inserting an instrument such as a treatment instrument is formed from the tip end of the endoscope insertion part 12 to the inside the endoscope manipulation part 14. The insertion channel 25 serves as a channel for both air feed and suction. A tip end of the insertion channel 25 is open in the tip end structure 15, and forms an opening 26 for suction and air feed and for allowing the treatment instrument to protrude. Inside the endoscope manipulation part 14, the insertion channel 25 is branched into a channel 27 in a side of an insertion port for the treatment instrument, and a channel 28 in a side of an endoscopic fluid control apparatus 30 described later. The channel 27 of the treatment instrument is connected to an insertion port 29 for inserting the treatment instrument, etc. The channel 28 in the side of the fluid control apparatus 30 is connected to an attachment part 32. The endoscopic fluid control apparatus 30, described later, is detachably attached to the attachment part 32.

Figure 2:
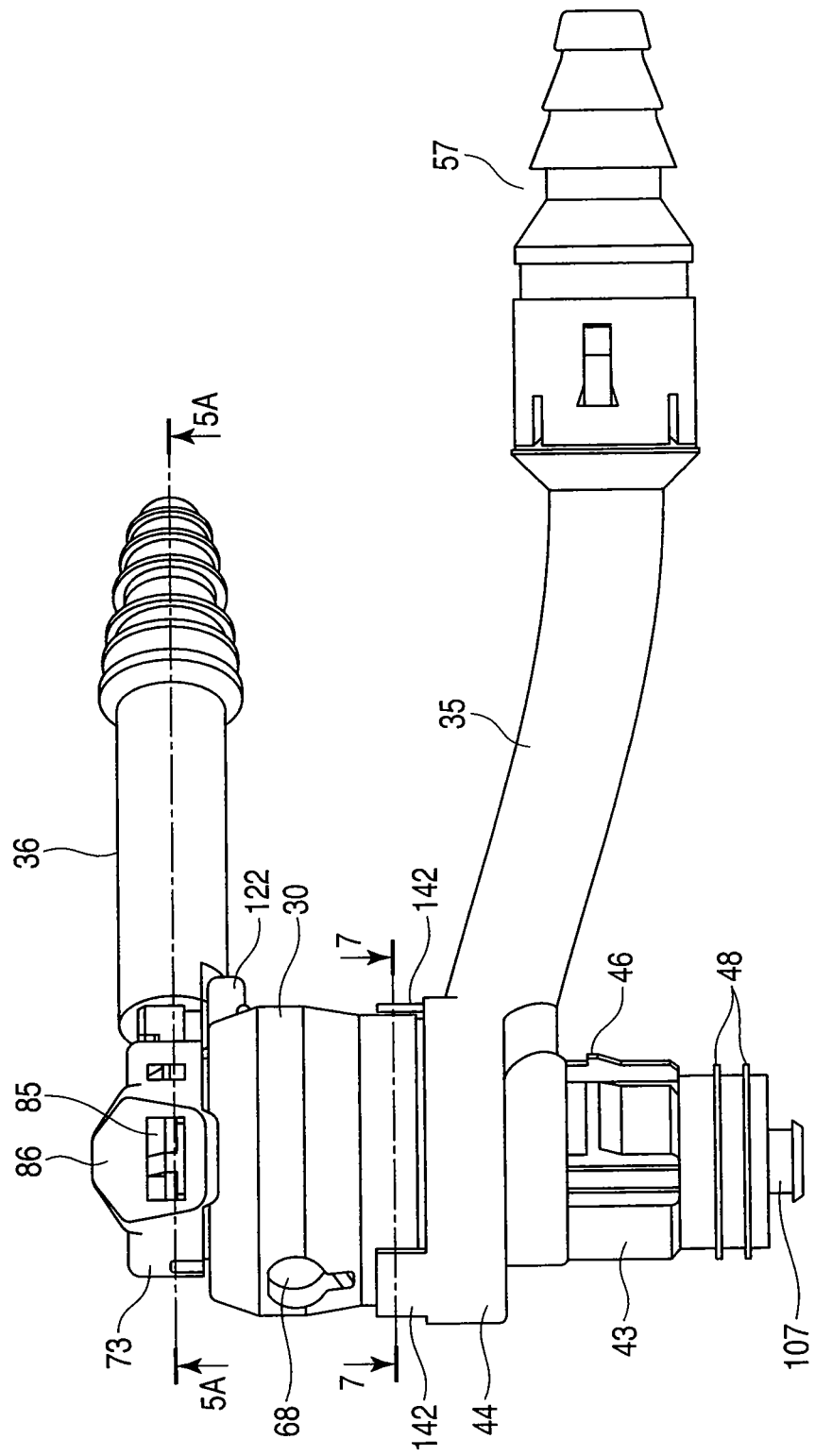
FIG. 2 is a side view of a fluid control apparatus of the endoscope.

FIG. 2 is a side view of the fluid control apparatus 30. The fluid control apparatus 30 is provided with the metal suction mouthpiece (suction-tube connection port part) 35 and the metal air-feed mouthpiece (air-feed-tube connection port part) 36. As illustrated in FIG. 1, a suction tube 38 is connected to the metal suction mouthpiece 35, and an air-feed tube 39 is connected to the metal air-feed mouthpiece 36. A protruding tip end of the suction tube 38 is detachably connected to a suction device such as an unillustrated suction pump. The suction tube 38 is a suction channel communicating with the insertion channel 25 and channel 28 which constitute one channel. A protruding tip end of the air-feed tube 39 is detachably attached to an air-feed device such as an unillustrated air-feed pump.

Next, the fluid control apparatus 30 will be specifically described. The fluid control apparatus 30 has a structure configured as a single valve device, into which a suction control valve mechanism and an air-feed control valve mechanism are integrally assembled, and the structure is attachable/detachable to/from the endoscope 10.

Figure 3:
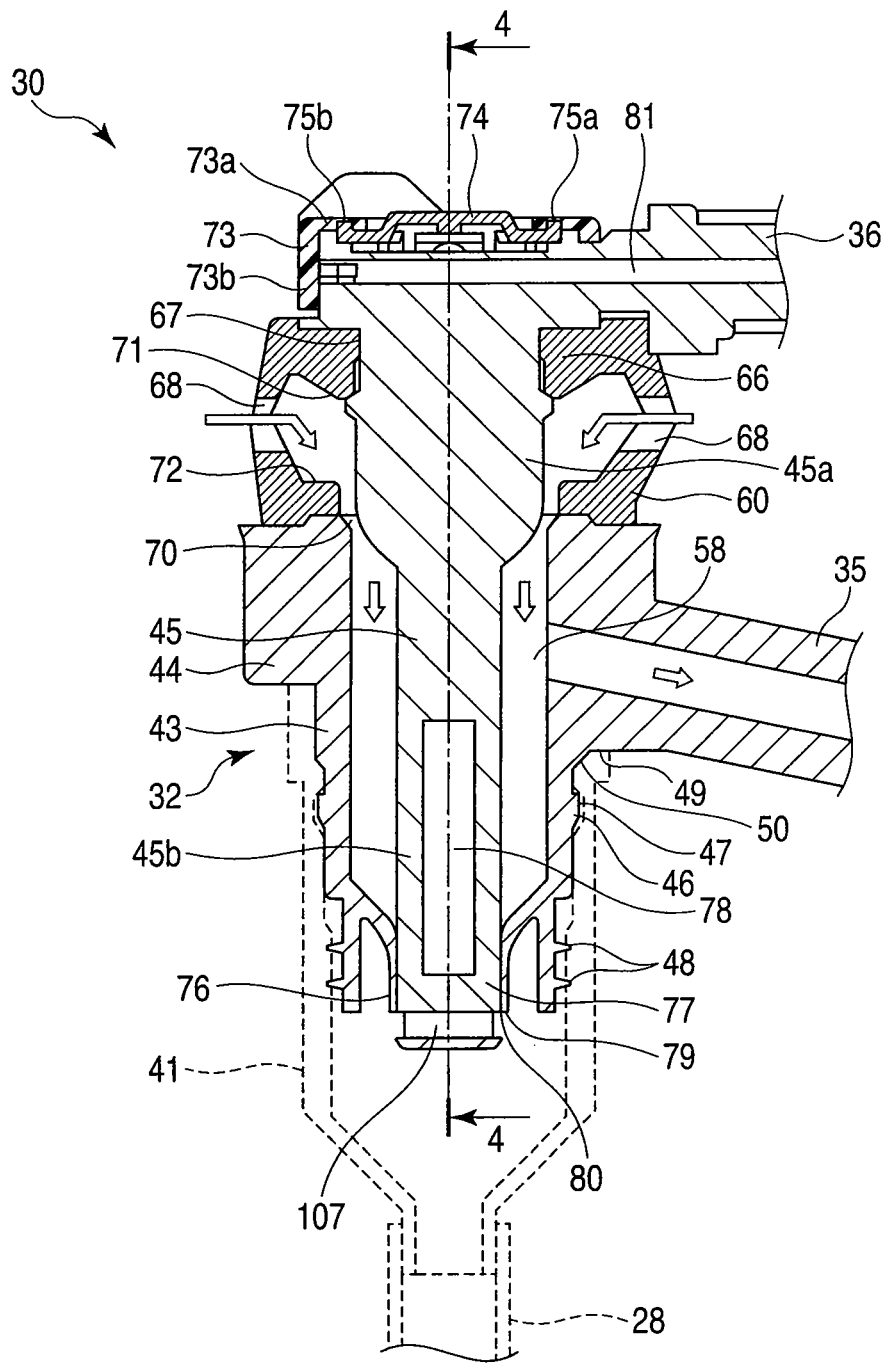
FIG. 3 is a longitudinal sectional view illustrating the fluid control apparatus longitudinally cut along a plane along centers of a suction base metal and a metal air-feed mouthpiece (along a line 3-3 in FIG. 5A)

As illustrated in FIG. 3, the attachment part 32 to which the fluid control apparatus 30 is attached comprises a circular attachment tube 41 provided on the endoscope manipulation-part body 23. The attachment tube 41 is fixed to the endoscope manipulation-part body 23. A top end of the attachment tube 41 faces a side of an outer surface of the endoscope manipulation-part body 23, and opens to the exterior. An inner end (lower end) of the attachment tube 41 is positioned inside the endoscope manipulation-part body 23 and is connected to the channel 28.

As illustrated in FIG. 3, the fluid control apparatus 30 comprises a cylinder 43 having a substantially circular tube shape such as a valve device body, and a piston body 45 provided inside the cylinder 43. The fluid control apparatus 30 controls suction from the insertion channel 25 by pushing in the piston body 45 with a finger. A lower end of the cylinder 43 is detachably engaged into (attached to) the attachment tube 41. The cylinder 43 is attached to the attachment part 32 (attachment tube 41) in a manner such that the top end of the cylinder 43 is exposed to the exterior of the attachment tube 41. Specifically, a flange 44 which is thicker than an inner diameter of the attachment tube 41 is formed on an outer circumference of the cylinder 43. This flange 44 makes contact with an outer end surface of the attachment tube 41, thereby defining an insertion attachment position of the cylinder 43 in relation to the attachment tube 41.

As illustrated in FIG. 3, an inner circumferential wall surface of the attachment tube 41, and an outer circumferential wall surface of the cylinder 43 engaged in the attachment tube 41 are provided with engagement parts which mutually engage with each other. The engagement parts comprise a convex 46 formed on either one of the outer circumferential wall surface of the cylinder 43 and the inner circumferential wall surface of the attachment tube 41, and a concave 47 formed on the other one of the outer circumferential wall surface of the cylinder 43 and the inner circumferential wall surface of the attachment tube 41. As the convex 46 and concave 47 engage with each other, the attachment tube 41 supports (holds) the cylinder 43. The convex 46 and concave 47 are provided so as to extend over a whole circumference of the attachment tube 41 or the cylinder 43 about an axis thereof. A sealing protrusion 48 which seals an inward part of the attachment tube 41 from outside is provided on an outer circumference of the lower end of the cylinder 43. The sealing protrusion 48 is provided to extend over the whole circumference of the cylinder 43 about an axis thereof. Further, a ring-shaped gasket (unillustrated) is attached to an outer circumferential part of the cylinder 43 engaged in the attachment tube 41. In this manner, much tighter sealing is achieved between the engagement parts of the attachment tube 41 and cylinder 43. In this manner, the cylinder 43 is maintained to be air-tight to the attachment tube 41. Further, the cylinder 43 can rotate about its own center axis while maintaining a sealed state. Further, the cylinder 43 is fixedly held by the attachment tube 41, owing to an engagement force and a friction force with respect to the attachment tube 41.

As illustrated in FIGS. 3 and 8A, a cam part 49 having a convex shape and protruding downward is formed at a part of a lower surface of the flange 44. The part of the lower surface of the flange 44 means, for example, a part positioned below the metal suction mouthpiece 35. As illustrated in FIG. 3, a cam receiving part 50 is formed at an edge of a top end of the attachment tube 41 which is opening. The cam receiving part 50 is an engagement part opposed to the cam part 49, is to be engaged with the cam part 49, and has a concave shape. The cam part 49 and cam receiving part 50 function as a cam mechanism which assists in detaching the cylinder 43 when the cylinder 43 is detached from the attachment tube 41. When the fluid control apparatus 30 is attached to the attachment tube 41, the cylinder 43 is engaged into the attachment tube 41 in a predetermined direction. Then, the cam part 49 engages with the cam receiving part 50, and the cylinder 43 is attached at a predetermined position relative to the attachment tube 41, as illustrated in FIG. 3. When the fluid control apparatus 30 is detached from the attachment tube 41, the cam part 49 takes off (detaches) from the cam receiving part 50 and pulls up the attachment tube 41 from the cylinder 43, as the cylinder 43 rotates about its axis. Accordingly, the cylinder 43 can be easily detached from the attachment tube 41.

As illustrated in FIGS. 2 and 3, the metal suction mouthpiece 35 is formed on the flange 44 in a substantially circular tube shape to be integral with the cylinder 43. The metal suction mouthpiece 35 is protruded toward a side of the cylinder 43. A suction tube connection part 57 for connecting the suction tube 38 is provided at a tip end of the metal suction mouthpiece 35.

Further, as illustrated in FIG. 3, a suction channel 58 as a first channel is formed inside the cylinder 43 and an inner hole of the metal suction mouthpiece 35. That is, the cylinder 43 comprises the first channel (suction channel 58) which transfers fluid to the insertion channel 25.

Figure 4:
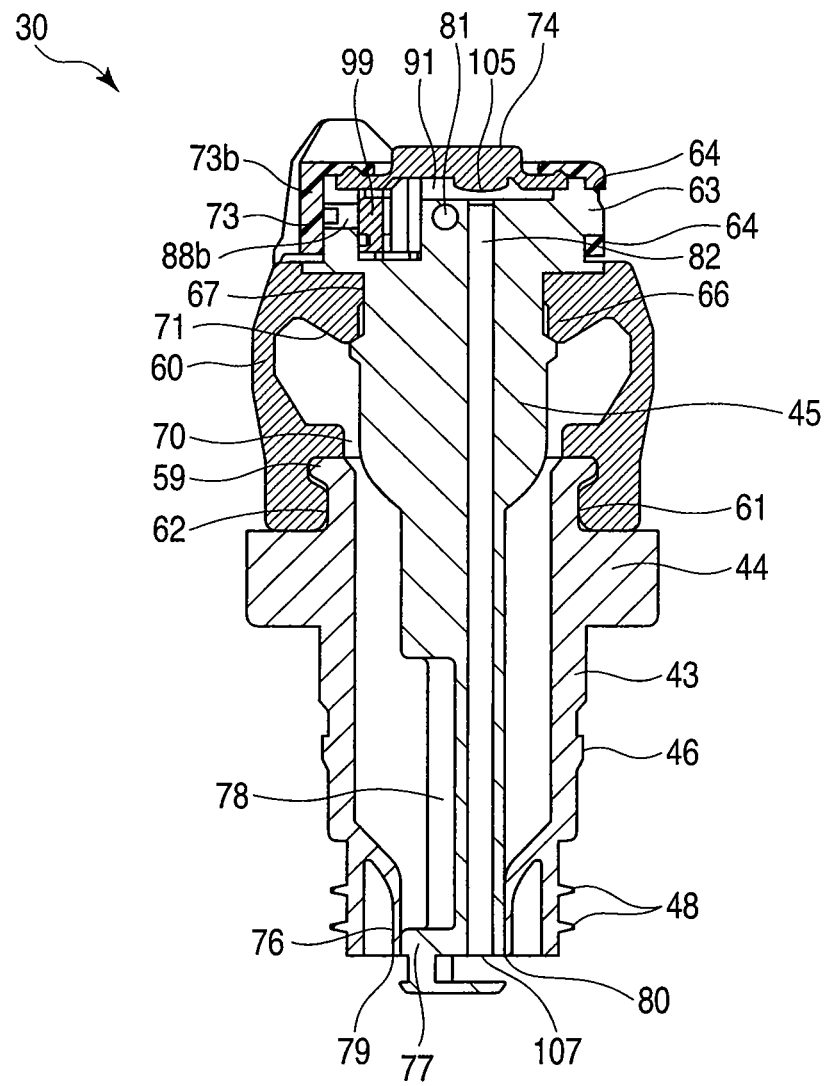
FIG. 4 is a longitudinal sectional view illustrating the fluid control apparatus longitudinally cut along a plane perpendicular to the plane along the centers of the suction base metal and metal air-feed mouthpiece (along a line 4-4 in FIG. 3)

As illustrated in FIG. 4, the top end of the cylinder 43 engages with a lower end of an elastic member 60. Specifically, a circular connection part 59 having a smaller diameter than the flange 44 is formed at the top end of the cylinder 43. A concave 61 extended over the whole circumference of the cylinder 43 about an axis thereof is formed in an outer circumference of the connection part 59. The elastic member 60 is formed of elastic rubber into a substantially cylindrical shape. A convex 62 extended over a whole circumference of the elastic member 60 about an axis thereof is formed on an inner circumferential surface of the lower end of the elastic member 60. Further, the convex 62 is engaged into the concave 61. Therefore, an opening part at the lower end of the elastic member 60 is covered and engaged on the outer circumference of the connection part 59. The elastic member 60 air-tightly connects with the cylinder 43. Further, the lower end of the elastic member 60 engages with the top end of the cylinder 43, with the lower end thereof sealed in tight contact with the cylinder 43. The lower end of the elastic member 60 is also fixedly attached to the cylinder 43, with the lower end sealed in tight contact with the cylinder 43. At this time, the lower end of the elastic member 60 is attached to the top end of the cylinder 43, with the lower end of the elastic member 60 positioned coaxial to the cylinder 43.

As illustrated in FIG. 3, the elastic member 60 is shaped in a substantially cylindrical shape. A center part of the top end of the elastic member 60 is open. The piston body 45 attached to the cylinder 43 is inserted into the elastic member 60 so as to penetrate upward into the elastic member 60. A convex 66 is formed on an inner circumferential surface of the top end of the elastic member 60. The convex 66 is provided so as to protrude inward and extend over the whole circumference of the elastic member 60 about an axis thereof. Further, a concave 67 is formed in an outer circumference of the top end of the piston body 45. The concave 67 is provided so as to extend over the whole circumference of the cylinder 43 about the axis thereof. As the convex 66 is engaged in the concave 67, the top end of the elastic member 60 engages with the top end of the piston body 45, with both top ends sealed in tight contact with each other. The top end of the elastic member 60 is fixedly secured to the piston body 45.

Figure 8B:
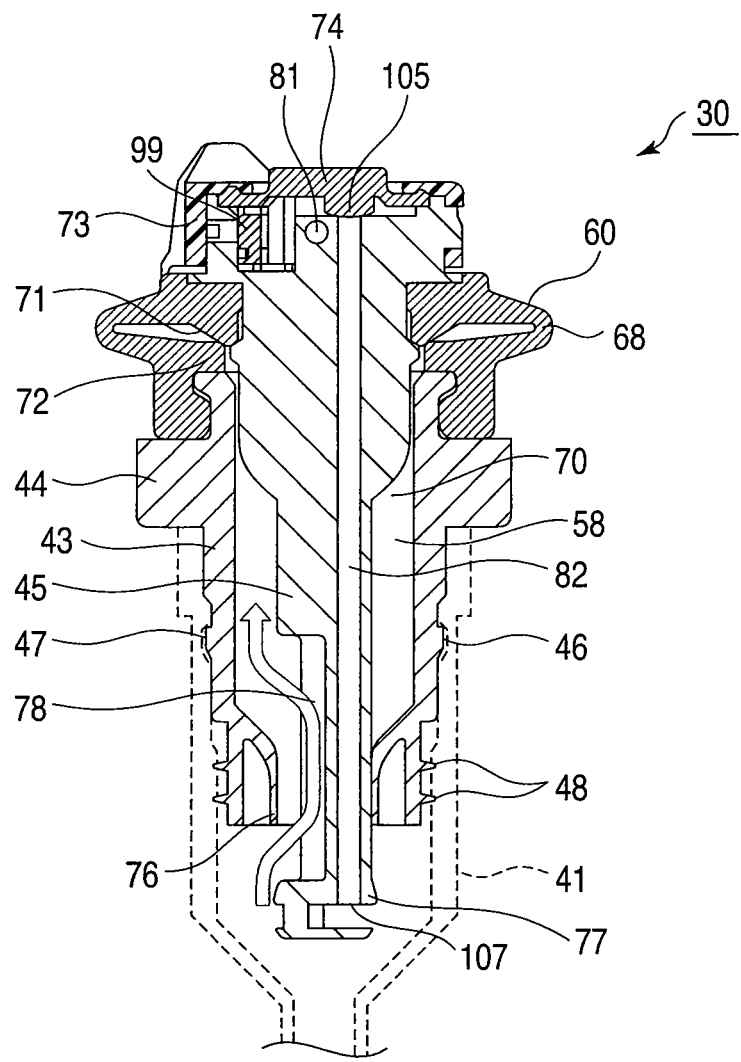
FIG. 8B is a longitudinal sectional view illustrating the fluid control apparatus, longitudinally cut along the plane along the line 4-4 in FIG. 3 during suction.
Figure 8C:
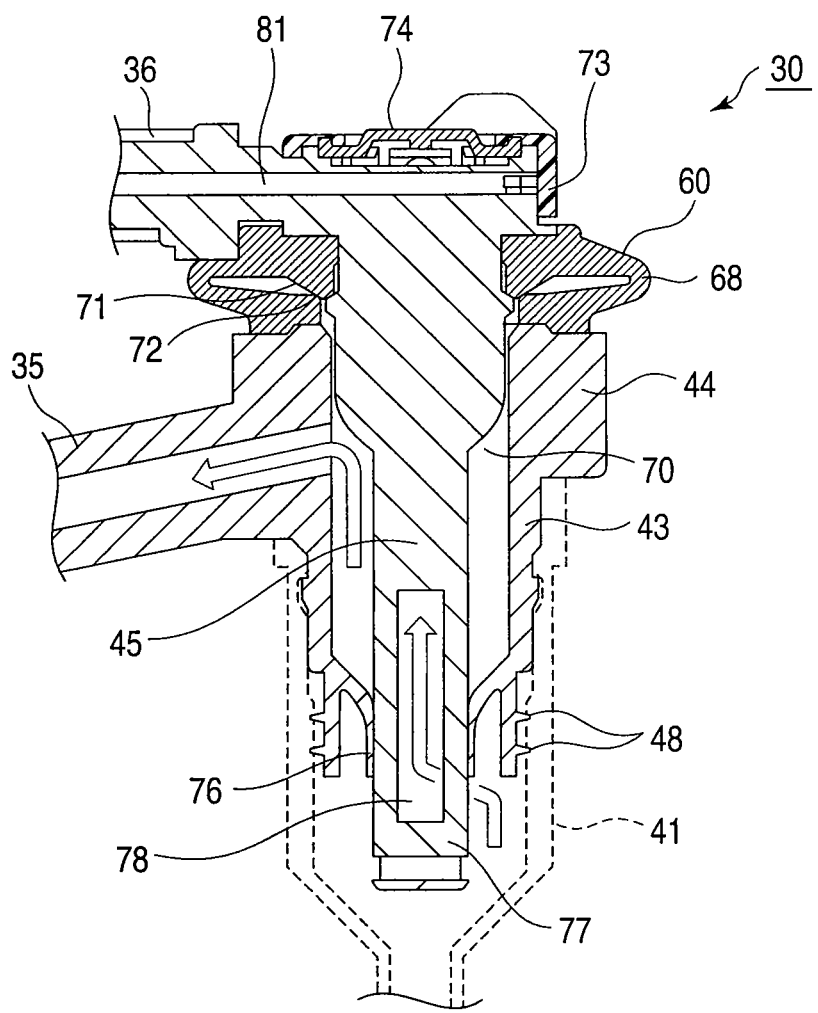
FIG. 8C is a longitudinal sectional view illustrating the fluid control apparatus, longitudinally cut along the plane along the line 3-3 in FIG. 5 during suction.

As illustrated in FIGS. 8A, 8B, and 8C, a side wall part of a middle part of the elastic member 60 is folded so as to protrude outward, and forms a spring member which can be elastically compressed and deformed in axial directions. Further, as illustrated in FIG. 3, suction leak holes 68 which communicate with the inside of the cylinder 43 (the suction channel 58 as the first channel) are drill in the side wall part of the middle part of the elastic member 60. The suction leak holes 68 communicate with the suction channel 58, and take in air from outside into the cylinder 43. Here, plural or, for example, two suction leak holes 68 are provided symmetrically in relation to a center of the elastic member 60. Further, one of the suction leak holes 68 is positioned, as illustrated in FIG. 3, between the metal suction mouthpiece 35 and the metal air-feed mouthpiece 36, at the same side portion as the metal suction mouthpiece 35 and the metal air-feed mouthpiece 36. As illustrated in FIGS. 8A, 8B, and 8C, when the elastic member 60 is pushed in together with the piston body 45, the side wall part in the middle part where the suction leak holes 68 are formed are folded so as to protrude outward. The suction leak holes 68 are thereby substantially closed. As illustrated in FIG. 3, the lower end of the elastic member 60 has a cylindrical shape, and a center part of the lower end is open. The lower end engages with the top end of the cylinder 43. Further, as described previously, the elastic member 60 also has a cylindrical shape, and a center part of the top end is open. The opening part engages with an outer circumference of the piston body 45.

As illustrated in FIGS. 3 and 4, in the opening part of the center part of the top end of the elastic member 60, a sealing surface 71 is formed on an inner surface of a top end wall part, which makes contact with the opening part and is adjacent to the opening part, so as to turn around a circumferential edge of the opening part about an axis thereof. The sealing surface 71 protrudes in a downward axis direction and has a tapered shape which is inclined in an inward radial direction. Further, in the opening part of the center part of the lower end of the elastic member 60, an edge part 72 is formed on an inner surface which is adjacent to the opening part. The edge part 72 protrudes so as to turn around along the circumferential edge of the opening part about an axis thereof. As illustrated in FIGS. 8A, 8B, and 8C, when the elastic member 60 is compressed, the sealing surface 71 makes contact with the edge part 72. Further, the sealing surface 71 and edge part 72 shut off communication between inside of the cylinder 43 (the suction channel 58 as the first channel) and outside of the elastic member 60 (the suction leak holes 68). The sealing surface 71 and edge part 72 function as a valve which opens/closes at the time of suction operation.

Thus, the elastic member 60 holds the piston body 45 to be movable relatively to the cylinder 43 between the position where the suction channel 58 is closed and the position where the suction channel 58 is opened.

As illustrated in FIG. 3, the piston body 45 is formed by a member having a substantially circular columnar shape. The piston body 45 is provided in a state in which the piston body 45 substantially penetrates both of the elastic member 60 and the cylinder 43. The top end of the piston body 45 is provided so as to protrude upward from the opening part in the top end of the elastic member 60. A cover member 73 which covers a side circumferential edge of the top end of the piston body 45 is provided to cover the top end of the piston body 45 protruding from the top end of the elastic member 60. A center of the cover member 73 is open. A top end surface of the piston body 45 corresponding to the opening part is covered with an operation button (operation member) 74. The operation button 74 is a member separate from the cover member 73, and constitutes a suction manipulation part. The operation button 74 is formed of a substantially disc-like elastic member in a film-like shape. This elastic member is made of, for example, an elastic material such as rubber or thermoplastic resin. As illustrated in FIG. 3, a convex 75a is provided on an upper surface of an outer circumferential edge of the operation button 74, over a whole circumference thereof. A concave 75b is provided in a lower surface of an inner circumferential edge of the cover member 73, over a whole circumference thereof.

The convex 75a engages with the concave 75b from below, thereby air-tightly connecting the cover member 73 and the operation button 74 to each other. Further, parts of the cover member 73 and operation button 74 may be fixed to each other by bonding. Although details will be described later, the cover member 73 is provided on the piston body 45. Therefore, the operation button 74 is provided, by the cover member 73, on the piston body 45 as an insertion member into which a second divisional air-feed channel 82 is inserted.

By pressing the operation button 74 or by releasing a pressure thereon, the piston body 45 can be moved in axial directions, relative to the cylinder 43, while receiving an elastic force of the elastic member 60. The elastic member 60 comes to have an elastic compression force and an elastic energizing recovery force as the piston body 45 moves. The elastic member 60 deforms in accordance with movement of the piston body 45. That is, as illustrated in FIG. 3, the suction leak holes 68 are open in a non-operational state in which the operation button 74 is not operated (this position is also referred to as a leak position). Further, as illustrated in FIGS. 8A, 8B, and 8C, when the operation button 74 is pressed and operated and the elastic member 60 is compressed, the suction leak holes 68 are substantially deformed to thereby bring the sealing surface 71 and the edge part 72 into contact with each other, thereby closing the space therebetween (this position is also referred to as a suction position).

The piston body 45 comprises a large diameter part 45a in a side of the top end thereof, and a small diameter part 45b in a side of the lower end thereof, as illustrated in FIG. 3. When the piston body 45 is at a non-operational position as illustrated in FIG. 3, the large diameter part 45a is located substantially outside the cylinder 43. An outer diameter of the large diameter part 45a is smaller than a diameter of the opening part of the center part of the lower end of the elastic member 60. Therefore, a gap is formed between the large diameter part 45a and the lower end of the elastic member 60. Therefore, as illustrated in FIG. 3, when the piston body 45 is at the non-operational position, a suction leak channel 70 which connects the inside of the cylinder 43 (the suction channel 58 as the first channel) to the suction leak holes 68 is formed in the gap formed between the large diameter part 45a and the lower end of the elastic member 60.

Further, as illustrated in FIG. 3, a valve body 77 which cooperates with a valve seat 76 formed at the lower end of the cylinder 43 is provided at the lower end of the piston body 45. The valve seat 76 and the valve body 77 form a valve part which closes when suction is not performed. The lower end of the cylinder 43 has a tapered shape which is slightly inclined downward from an inner circumferential surface in an axial direction and inward in a radial direction. In the tapered part, the lower end has a cylindrical shape which has a small diameter and is coaxial to the cylinder 43. The valve seat 76 is formed on the cylindrical inner surface. Further, as illustrated in FIG. 3, when the piston body 45 is at the non-operational position (leak position), the valve body 77 is provided inside the valve seat 76, and seals an inner hole of the valve seat 76. In addition, the valve body 77 together with the valve seat 76 shuts off the inside of the attachment tube 41 inside of the cylinder 43 (the suction channel 58 as the first channel) from each other. That is, the suction channel 58 closes.

As illustrated in FIGS. 8A, 8B, and 8C, when the piston body 45 is pressed to the suction position, the valve body 77 is positioned below the valve seat 76, at the release position indicating a position inside the attachment tube 41. At this time, the inside of the attachment tube 41 and inside of the cylinder 43 (the suction channel 58 as the first channel) communicate with each other. That is, the suction channel 58 opens.

That is, the piston body 45 comprises a valve part (valve body 77) which is movable relative to the cylinder 43 between a position where the suction channel 58 is opened relative to the insertion channel 25 and a position where the suction channel 58 is closed relative to the insertion channel 25.

As illustrated in FIGS. 3 and 4, a guide part 78 shaped like a concave groove is formed in a side wall of the piston body 45 above the valve body 77. The guide part 78 extends in an axial direction of the piston body 45 from a top end of the valve body 77. As illustrated in FIG. 3, when the piston body 45 is at the non-operational position, the entire guide part 78 is located in the cylinder 43. As illustrated in FIGS. 8A, 8B, and 8C, when the piston body 45 is pushed in to the suction position, the guide part 78 is located over the whole valve seat 76 from below to above the valve seat 76, and makes the inside of the attachment tube 41 and the inside of the cylinder 43 (the suction channel 58 as the first channel) communicate with each other to make a suction force act on the channel 28. That is, the guide part 78 makes the inside of the attachment tube 41 and the inside of the cylinder 43 (the suction channel 58 as the first channel) communicate with each other. The valve body 77 cooperates with the valve seat 76 to constitute a valve part which opens/closes the suction channel 58 as the first channel, in accordance with a moving position of the piston body 45.

As illustrated in FIG. 3, a limiter part 80 is formed on an outer circumferential surface of the lower end of the piston body 45. The limiter part 80 makes contact with a limit surface 79 constituted by a lower end surface of the valve seat 76, thereby limiting upward movement of the piston body 45. The limiter part 80 as described above is a large diameter part protruded in radial directions of the lower end of the piston body 45. Further, as illustrated in FIG. 3, when the piston body 45 is at the non-operational position where upward movement of the piston body 45 is limited, the limiter part 80 makes contact with the limit surface 79 thereby to limit upward movement of the piston body 45. When the piston body 45 is at the non-operational position where upward movement is limited, the elastic member 60 is slightly compressed/deformed in axial directions thereof. In other words, a termination end to which the piston body 45 is moved upward by an energizing force of the elastic member 60 is a position illustrated in FIG. 3, to which upward movement of the piston body 45 is limited by contact of the limiter part 80 with the limit surface 79. As illustrated in FIG. 3, when the piston body 45 is at the non-operational position, a suction leak state is created in which the suction leak holes 68 communicate with the metal suction mouthpiece 35 through a suction leak channel 70. Further, as illustrated in FIGS. 8A, 8B, and 8C, when the piston body 45 is pressed, the suction leak channel 70 closes, and the suction tube 38 is accordingly put in a suction state in which the suction tube 38 communicates with the attachment tube 41 and channel 28 through the metal suction mouthpiece 35, suction channel 58, and guide part 78. That is, the valve seat 76, valve body 77, limit surface 79, and limiter part 80 constitute a suction control mechanism.

Next, an air-feed control mechanism of the fluid control apparatus 30 will be described. As illustrated in FIG. 5A, a first divisional air-feed channel 81 which communicates with the inner hole of the metal air-feed mouthpiece 36 is provided at the top end of the piston body 45, so as to cross the top end. Further, as illustrated in FIG. 4 and FIG. 5A, a second divisional air-feed channel 82 is provided in the piston body 45, so as to penetrate the piston body 45 along vertical axis directions thereof. The piston body 45 is an insertion member into which the second divisional air-feed channel 82 is inserted. The first divisional air-feed channel 81 and second divisional air-feed channel 82 are provided in the piston body 45, so as to neither encounter each other nor directly cross each other. The first divisional air-feed channel 81 and second divisional air-feed channel 82 constitute a second channel which communicates with the metal air-feed mouthpiece 36 connecting the air-feed tube 39. That is, the piston body 45 comprises the first divisional air-feed channel 81 and second divisional air-feed channel 82, constituting a second channel which transfers fluid from the connection port part (the metal air-feed mouthpiece 36) to the insertion channel 25. Further, the piston body 45 comprises a connection port part (the metal air-feed mouthpiece 36) for connecting a fluid tube (the air-feed tube 39).

As illustrated in FIG. 5A, the first divisional air-feed channel 81 linearly communicates with the inner hole of the metal air-feed mouthpiece 36. A first communication channel 84 is formed in the side wall surface of the top end of the piston body 45. The first communication channel 84 is a groove-like notch (opening) along a circumferential direction of the piston body 45 covered with the cover member 73. The first divisional air-feed channel 81 is connected to the first communication channel 84, crossing the top end of the piston body 45. The first communication channel 84 is covered with the cover member 73, and is formed along the circumferential direction of the piston body 45 in this state. The first communication channel 84 is open toward the air-feed leak hole 85 described later. The first communication channel 84 is arranged in a manner such that the opening thereof is oriented to face the air-feed leak hole 85 and penetrates to the exterior. Therefore, resistance of air flow which leaks from the air-feed leak hole 85 decreases and improves the air-feed leak performance.

As illustrated in FIGS. 3 and 4, the cover member 73 is made of an elastic material, such as rubber or thermoplastic resin. The cover member 73 comprises an annular part 73a which covers a peripheral part of a top surface of the piston body 45, and an annular part 73b which covers a top end of a side surface of the piston body 45. The annular parts 73a and 73b are attached so as to tightly engage with the peripheral part of the top end of the piston body 45. Further, as illustrated in FIGS. 4 and 5A, a protrusion 63 is provided on the side surface of the top end of the piston body 45. A hole 64 corresponding to the protrusion 63 is provided in the cover member 73. As the protrusion 63 is engaged into the hole 64, the cover member 73 is fixedly attached to and made to be in contact with the piston body 45.

As illustrated in FIG. 5A, a finger receiver surface 86 is formed on a circumferential edge of the cover member 73. An air-feed leak hole 85 for releasing the first communication channel 84 to the exterior is provided in the finger receiver surface 86. To facilitate operation, the finger receiver surface 86 is formed so as to face the piston body 45 in press axis directions, and to be oriented downward obliquely to the press axis directions. In this manner, there is avoided that the piston body 45 is pressed under a pressing force when a finger is placed on the finger receiver surface 86. Further, a pad of the finger is put on the finger receiver surface 86, and the air-feed leak hole 85 closes accordingly. Then, leakage of a gas from the first communication channel 84 is shut off. In addition, a leakage rate of the gas can be adjusted depending on an extent to which the air-feed leak hole 85 is closed with the finger.

As illustrated in FIG. 5A, a second communication channel 88 which communicates with the first communication channel 84 through the air-feed leak hole 85 is formed at the top end of the piston body 45. The second communication channel 88 is provided in a side opposite to the first communication channel 84 in relation to the air-feed leak hole 85 interposed therebetween. Further, a direction of a flow path toward the air-feed leak hole 85 from the first communication channel 84 and a direction of a flow path toward the second communication channel 88 from the air-feed leak hole 85 cross each other. The air-feed leak hole 85 is formed near a cross point between both directions. The first communication channel 84 and second communication channel 88 cross each other at the air-feed leak hole 85, and are formed to be oriented in opposite directions to each other. Therefore, the direction of the flow path from the first communication channel 84 toward the air-feed leak hole 85 is a direction which penetrates the air-feed leak hole 85 directly to the exterior. The second communication channel 88 is formed to extend from the exterior to the inside of the air-feed leak hole 85. When the air-feed leak hole 85 is closed by an obstacle such as a finger, the obstacle can be assumed to be, namely, a mirror. In this case, light traveling from the first communication channel 84 toward the air-feed leak hole 85 is reflected by the obstacle. The first communication channel 84 and second communication channel 88 are formed in a manner such that a flow-in end of the second communication channel 88 is positioned in a reflecting direction thereof. That is, the first communication channel 84 and the second communication channel 88 are provided, in respectively opposite sides, with the air-feed leak hole 85 intervened therebetween in a manner such that the channels are reversed and bent by the air-feed leak hole 85. Further, the first communication channel 84 and second communication channel 88 are located in a manner such that an angle between a flow path from the first communication channel 84 toward the air-feed leak hole 85 and a flow path from the air-feed leak hole 85 toward the second communication channel 88 is substantially 90°. The air-feed leak hole 85 is positioned at this reverse point.

Further, as illustrated in FIG. 5A, the second communication channel 88 comprises an upstream groove 88a formed on an outer surface of the top end of the piston body 45, and a downstream hole 88b drill in the top end of the piston body 45. The downstream hole 88b is continuous to a concave hole 89 formed in the outer surface of the top end of the piston body 45. As illustrated in FIG. 4, the hole 89 is formed so as to communicate with a third communication channel 91 which is formed between the top end surface of the piston body 45 and an inner surface of the operation button 74. Further, the third communication channel 91 communicates with the first communication channel 84 through the second communication channel 88 and air-feed leak hole 85, and also communicates with the second divisional air-feed channel 82 in a manner described later.

As illustrated in FIGS. 3, 4, and 5A, the air-feed tube 39, the first divisional air-feed channel 81, first communication channel 84, air-feed leak hole 85, second communication channel 88, third communication channel 91, and second divisional air-feed channel 82 constitute an air-feed channel which communicates with the insertion channel 25 and channel 28, as one channel.

As illustrated in FIGS. 5A and 5B, a check valve 95 as a first valve which stops backflow of fed air is provided between the second communication channel 88 and the third communication channel 91. That is, the check valve 95 as the first valve is provided on the air-feed channel described above, and opens only when feeding air. The check valve 95 comprises a valve seat 96 formed on a wall surface of the second communication channel 88 in the hole 89, an elastic member 97 engaged in the hole 89, and a valve body 99 formed by cutting a notch 98 in the elastic member 97. As illustrated in FIG. 5B, the notch 98 is cut in the elastic member 97 into a shape like an arc or "C", which partially acts as a hinge 94, thereby forming the valve body 99 in a shape like a flap. The elastic member 97 is engaged in the hole 89 which is drill in the top end surface of the piston body 45. The valve seat 96 is positioned in an upstream side of the air-feed flow, so as to face a valve body 99 positioned in a downstream side thereof, and puts the valve body 99 in a state of being elastically pushed into contact with the valve seat 96. Accordingly, the check valve 95 does not hinder air-feed flow in a forward direction but hinders only air-feed flow in a backward direction.

As illustrated in FIG. 5B, the valve body 99 is substantially C-shaped. The valve body 99 has a greater surface area than the notch 98. When backward flow occurs at the check valve 95, a fluid pressure acting on the valve body 99 is greater than channel resistance of the notch 98, and the valve body 99 moves like a flap, to make contact with the valve seat 96. Accordingly, the check valve 95 does not hinder air-feed flow in a forward direction but hinders only air-feed flow in a backward direction.

The hinge 94 which supports the valve body 99 is positioned to be oriented in a direction of pushing in the piston body 45, i.e., in a lower side of the valve body 99. Therefore, when the piston body 45 is pushed in, a force of pushing down the piston body 45 is applied to the elastic member 97. Even if the elastic member 97 is deformed, the force of pressing down and influence from the deformed elastic member 97 hardly transfer to the valve body 99 through the hinge 94. Further, a pressure applied to the elastic member 97 is received by a bottom surface of the hole 89, and is therefore shut off and hardly transfers to the valve body 99. Therefore, the valve body 99 is neither compressed nor twisted; and an open/close operation of the valve body 99 is stabilized by pushing in the piston body 45.

As illustrated in FIGS. 3, 4, and 5A, the check valve 95 as the first valve is positioned in an upstream side of air-feed than a valve body part 105 as a second valve, in the first divisional air-feed channel 81, first communication channel 84, air-feed leak hole 85, second communication channel 88, third communication channel 91, and second divisional air-feed channel 82, as an air-feed channel. In this manner, a suctioned material is prevented from flowing into the air-feed channel in a side of the air-feed tube.

The valve body 99 is provided on the piston body 45 as the insertion member.

As illustrated in FIG. 3, the top end surface of the piston body 45 is covered to be air-tight to the exterior by the cover member 73 and operation button (operation member) 74. Further, when the operation button 74 illustrated in FIGS. 3 and 4 is not pushed in, a third communication channel 91 is maintained in a gap between an inner surface of the operation button 74 and the top end surface of the piston body 45, on an inner surface of the operation button 74, as illustrated in FIG. 4. The third communication channel 91 communicates with the second divisional air-feed channel 82 which is open, at one end, in the top end of the piston body 45.

Further, as illustrated in FIG. 4, a valve device as the second valve capable of shutting off the third communication channel 91 and second divisional air-feed channel 82 when performing the suction operation is provided between the operation button 74 and the piston body 45. That is, as illustrated in FIG. 4, the operation button 74 comprises a convex valve body part 105 which faces the second divisional air-feed channel 82. The valve body part 105 as the valve device protrudes from the inner surface of the operation button 74. The valve body part 105 is apart from the second divisional air-feed channel 82 in a normal state in which the operation button 74 is not pushed in. When the operation button 74 is pushed in during a suction operation, the valve body part 105 makes contact with the second divisional air-feed channel 82, and closes the second divisional air-feed channel 82. The operation button 74 may directly close the second divisional air-feed channel 82 with the inner surface of the operation button 74, in place of the valve body part 105. That is, the operation button 74 may also serve as a valve body part (valve device). Thus, when the suction operation is performed, the inner surface of the operation button 74 or valve body part 105 closes the second divisional air-feed channel 82 as the operation button 74 is pushed in. Thus, the valve device (the valve body part 105 and operation button 74) as the second valve is provided on the operation button 74. When the operation button 74 is operated to perform suction operation, the valve device functions as a check valve which shuts off communication between the first divisional air-feed channel 81 as one of the air-feed channels and the second divisional air-feed channel 82 as the other of the air-feed channels, in the air-feed channel into which the operation button 74 is inserted.

Further, the valve device (valve body part 105) as the second valve is provided on the piston body 45 as the insertion member through the operation button 74. Further, as described previously, the valve body 99 and the valve body part 105 are provided on the piston body 45.

Here, when the operation button 74 is in the stand-by state, the gap is created between the inner surface of the operation button 74 and the top end surface of the piston body 45, as described previously. However, the inner surface of the operation button 74 may be brought into tight contact with the top end surface of the piston body 45 with a constant energizing force due to an elastic force of the operation button 74 itself. In this case, the operation button 74 is lifted up due to air pressure, thereby securely maintaining the third communication channel 91, and air can be fed from the third communication channel 91 to the second divisional air-feed channel 82. Further, if an air-feed pressure relatively lowers from a side of the first divisional air-feed channel 81 during suction or when the air-feed leak hole 85 is opened, the second divisional air-feed channel 82 is closed by the operation button 74, and the inner surface of the operation button 74 and the valve body part 105 advantageously function as a valve which shuts off communication between the first divisional air-feed channel 81 and the second divisional air-feed channel 82.

Thus, the inner surface of the operation button 74 and the valve body part 105 which serve also as a valve member are provided on the piston body 45, and shut off communication between the first divisional air-feed channel 81 and the second divisional air-feed channel 82.

Further, the valve body part 105 as the second valve is positioned in a downstream side of air-feed than the check valve 95 as the first valve, in the first divisional air-feed channel 81, first communication channel 84, air-feed leak hole 85, second communication channel 88, third communication channel 91, and second divisional air-feed channel 82, as the air-feed channel.

When the inner surface of the operation button 74 is brought into tight contact with the top end surface of the piston body 45 by an elastic force of the operation button 74 itself and air-feed is performed, the first divisional air-feed channel 81 and the second divisional air-feed channel 82 are once made to communicate with each other. Then, the pressure inside the operation button 74 suddenly decreases, and the operation button 74 contracts. Accordingly, the second divisional air-feed channel 82 is once closed by the operation button 74, and the air-feed pressure increases again. Then, the operation button 74 expands, and the second divisional air-feed channel 82 opens accordingly. Thus, expansion and contraction of the operation button 74 are repeated, and the operation button 74 then vibrates, thereby generating a sound. This sound changes depending on air-feed conditions such as an air-feed rate and an air-feed pressure. Therefore, operators can be made aware of an air-feed condition by sound, since such condition is difficult to comprehend visually.

As described previously, the second divisional air-feed channel 82 penetrates the piston body 45 in axial directions of movement of the piston body 45, as illustrated in FIG. 4. A lower end of the second divisional air-feed channel 82 forms an air-feed port 107 in a lower end surface of the piston body 45, as illustrated in FIG. 4. The air-feed port 107 is open so as to constantly communicate with the inside of the attachment tube 41. The air-feed port 107 is open perpendicularly to an extending direction of the insertion channel 25 at the lower end of the piston body 45. Therefore, it is difficult for a suctioned material to enter the second divisional air-feed channel 82.

As illustrated in FIG. 2, the suction tube connection part 57 for connecting the suction tube 38 is provided at a tip end of the metal suction mouthpiece 35.

Next, operation of the endoscopic device according to the present embodiment will be described. When the endoscope 10 is used, the fluid control apparatus 30 is attached to the attachment part 32, for preparation. At this time, as illustrated in FIG. 3, the cylinder 43 is inserted into the attachment tube 41 so as to match positions of the cam part 49 and the cam receiving part 50 with each other. Also as illustrated in FIG. 3, the fluid control apparatus 30 is attached to the attachment part 32 so as to engage the convex 46 and concave 47 with each other. Next, the suction tube connection part 57 is connected to an end of the suction tube 38, and the other end of the suction tube 38 is connected to an unillustrated suction device. Further, the metal air-feed mouthpiece 36 is connected to an end of the air-feed tube 39, and the other end of the air-feed tube 39 is connected to an unillustrated air-feed device.

Thus, when the fluid control apparatus 30 is attached to the attachment part 32, as illustrated in FIG. 8A, the finger receiver surface (air-feed operation surface) 86 where the air-feed leak hole 85 is open is located at a different position from the metal air-feed mouthpiece 36 to which the suction tube 38 is connected, and from the metal suction mouthpiece 35 to which the suction tube 38 is connected. Further, the finger receiver surface (air-feed operation surface) 86 is apart from the suction leak hole 68. As a result of this, the finger receiver surface (air-feed operation surface) 86 makes as little interference as possible with other constitutive members, and the air-feed leak hole 85 can therefore be easily operated by an operator's finger.

Next, a non-operational state of the fluid control apparatus 30 will be described. As illustrated in FIGS. 3, 4, and 5A, the fluid control apparatus 30 is in a stand-by state. When the suction device is driven, external air is taken in through the suction leak holes 68 into the fluid control apparatus 30 since the suction channel 58 and the suction leak channel 70 communicate with the suction leak holes 68. At this time, the valve part constituted by the valve seat 76 and valve body 77 is closed, and communication with the channel 28 (insertion channel 25) is shut off. Accordingly, suction from a side of the insertion channel 25 is prevented. Further, as denoted by arrows in FIG. 3, air taken in from the suction leak holes 68 is suctioned through the metal suction mouthpiece 35 and suction tube 38 by the suction device.

Further, when the air-feed device is driven, as denoted by an arrow in FIG. 5A, compressed air is fed into the metal air-feed mouthpiece 36 through the air-feed tube 39. The compressed air fed to the metal air-feed mouthpiece 36 flows from the first divisional air-feed channel 81 through the first communication channel 84 to the air-feed leak hole 85, and leaks to the exterior from the air-feed leak hole 85. Due to this leakage, an air-feed pressure at the air-feed leak hole 85 decreases, and the compressed air is therefore not fed to a side of the second communication channel 88. Thus, the compressed air is not fed to the side of the second communication channel 88, and the valve body 99 does therefore not open. Accordingly, the compressed air is not fed from the third communication channel 91 to the second divisional air-feed channel 82. Accordingly, air-feed to the insertion channel 25 is not performed.

Next, a description will be made of a case in which suction and air-feed are controlled by the fluid control apparatus 30. When the endoscope 10 is used, normally, the endoscope insertion part 12 is gripped by one hand, and the endoscope manipulation part 14 is gripped by the other hand. On the hand which grips the endoscope manipulation part 14, the endoscope grip part 22 is held by three fingers except a thumb and an index finger. The bend lever 24 is operated by the thumb of this hand, and the fluid control apparatus 30 is operated by the index finger of this hand. That is, the operation button 74 and air-feed leak hole 85 are operated by the index finger of the hand which grips and operates the endoscope manipulation part 14.

Figure 7A:
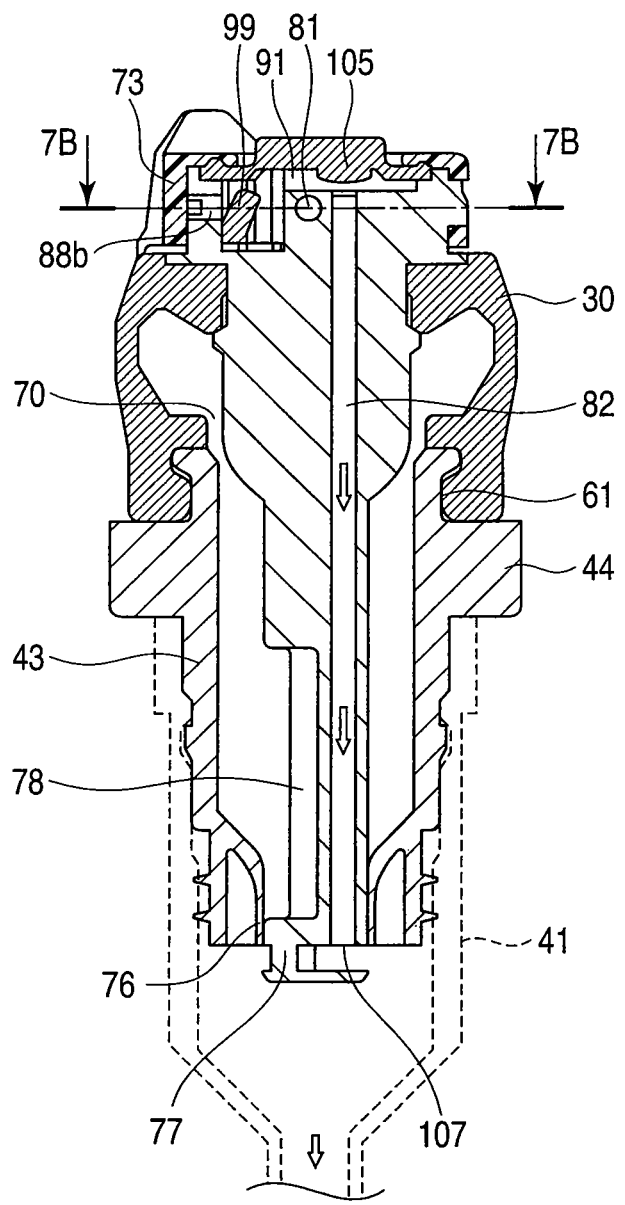
FIG. 7A is a longitudinal sectional view illustrating the fluid control apparatus, longitudinally cut along the plane along the line 4-4 in FIG. 3 during air feed.

At first, a description will be made of a case in which the fluid control apparatus 30 controls air-feed. As illustrated in FIG. 7B, a pad of the index finger is brought into contact with the finger receiver surface 86, thereby closing the air-feed leak hole 85. Then, a gas (compressed air) which has been leaking to the exterior through the air-feed leak hole 85 is shut off, and an air-feed pressure inside the air-feed leak hole 85 increases. In this manner, as denoted by an arrow in FIG. 7B, the gas is fed to the side of the second communication channel 88. The gas which has flowed to the side of the second communication channel 88 pushes and opens the valve body 99, as illustrated in FIG. 7A and is fed to the third communication channel 91 through the hole 89 illustrated in FIG. 7B. At this time, the operation button 74 is not pressed but floats under a pressure of the gas fed into the third communication channel 91, as illustrated in FIG. 7A, thereby forming the third communication channel 91. Further, the gas is fed to the second divisional air-feed channel 82 through the third communication channel 91. The gas fed into the second divisional air-feed channel 82 then flows to the insertion channel 25 from the air-feed port 107 through the inside of the cylinder 43 and attachment tube 41 and through the channel 28. Further, the gas flows from the channel opening 26 into the body cavity.

Next, a description will be made of a case in which the fluid control apparatus 30 controls suction. In this case, as illustrated in FIG. 8A, the operation button 74 is pushed in a direction denoted by an arrow P. The piston body 45 thereby moves down (to the suction position) relative to the elastic member 60 and the cylinder 43. Then, as illustrated in FIGS. 8B and 8C, the elastic member 60 is pushed and compressed, and the sealing surface 71 accordingly makes contact with the edge part 72. In this manner, the sealing surface 71 and the edge part 72 shut off communication between the inside of the cylinder 43 (the suction channel 58 as the first channel) and outside of the elastic member 60 (the suction leak hole 68). Further, during suction operation, the valve body part 105 closes the second divisional air-feed channel 82, and therefore, suction from the second divisional air-feed channel 82 to the sides of the first divisional air-feed channel 81 and air-feed leak hole 85 is prevented. At this time, the side wall part of the middle part of the elastic member 60 (near the suction leak hole 68) is folded so as to protrude outward. Therefore, the suction leak hole 68 itself is pushed and compressed (see FIGS. 8A, 8B, and 8C).

In this manner, at the same time as communication of the suction leak hole 68 with the exterior is shut off, the piston body 45 is pushed into the cylinder 43 by the operation button 74, as illustrated in FIG. 8B and FIG. 8C, and the valve body 77 penetrates to below the valve seat 76. The valve part constituted by the valve seat 76 and valve body 77 accordingly opens, and the inside of the cylinder 43 and inside of the attachment tube 41 communicate with each other. The guide part 78 is provided so as to bridge lower and upper parts of the valve seat 76, and therefore makes the insides of the cylinder 43 and attachment tube 41 communicate with each other. Accordingly, the insides of the cylinder 43 and attachment tube 41 communicate with each other, shut off from the exterior. Therefore, the metal suction mouthpiece 35 can suction, for example, liquid in a body cavity from the channel opening 26 through the insertion channel 25 and channel 28, in a direction denoted by arrows in FIGS. 8B and 8C. During this suction, the flap 162 of the suction tube connection part 57 opens and releases the suction channel.

Since the operation button 74 is pressed during suction, the valve body part 105 is pressed into contact with the second divisional air-feed channel 82, thereby shutting off the second divisional air-feed channel 82. In this manner, the first divisional air-feed channel 81 and the second divisional air-feed channel 82 are surely separated from each other. As a result of this, air-feed is not performed even if the air-feed leak hole 85 is closed by mistake. Further, even if a suctioned material enters the second divisional air-feed channel 82, the suctioned material is prevented from taking into the side of the first divisional air-feed channel 81, and prevented from entering into the metal air-feed mouthpiece 36, from being emitted through the air-feed leak hole 85, and from entering into the metal air-feed mouthpiece 36.

When the finger is released from the operation button 74 and suction is released, a liquid remaining in the insertion channel 25 flows into the cylinder 1 due to the inertia of the liquid itself. At this time, even if the liquid flows into the second divisional air-feed channel 82 under a negative pressure, the valve body 99 is closed, and suctioned material (liquid) therefore can be prevented from entering into the side of the air-feed leak hole 85, in the present embodiment. Accordingly, the suctioned material can be prevented from entering into a clean area in the side of the air-feed tube 39. That is, according to the present embodiment, even if the suctioned material enters the second divisional air-feed channel 82, the suctioned material is prevented from taking into the side of the first divisional air-feed channel 81, and can therefore be prevented from entering into the metal air-feed mouthpiece 36, being emitted from the air-feed leak hole 85, and entering into the metal air-feed mouthpiece 36.

Also according to the present embodiment, both of air feed and suction can be operated by one-finger operation for the insertion channel 25. Further, in the present embodiment, leakages are ensured for air-feed and suction in non-operational periods. In operation of each of air-feed and suction, interference between air-feed and suction, and backflow can be prevented.

Also in the present embodiment, the guide part 78 is located over the whole valve seat 76 from below to above the valve seat 76, and makes the insides of the attachment tube 41 and cylinder 43 (the suction channel 58 as the first channel) communicate with each other to make a suction force act on the channel 28. In this manner, in the present embodiment, a suction force can be maintained without reducing a suction force to a side of the channel 58 to which a suction force is desired to be applied.

In the present embodiment, when the metal air-feed mouthpiece 36 is connected to the suction tube 38 by mistake, an external gas is suctioned from the air-feed leak hole 85. Therefore, suction to a depth beyond the first divisional air-feed channel 81 is prevented. Further, when the air-feed leak hole 85 is closed by mistake, a pressure in the side of the first divisional air-feed channel 81 decreases, and the pressure in the second communication channel 88 decreases accordingly. As a result, the valve body 99 is pulled by the valve seat 96, thereby preventing the inside of the operation button 74 from being suctioned.

When the fluid control apparatus 30 is constituted by a disposable product, the fluid control apparatus 30 is detached from the attachment tube 41 after use of the endoscope 10. Only the endoscope 10 is subjected to cleaning. Therefore, an air-feed function and a suction function are prevented from interfering with each other, and the insertion channel 25 can be easily cleaned. Accordingly, work for cleaning/sanitizing channels inside the endoscope can be facilitated.

In the fluid control apparatus 30 described above, the valve device which shuts off communication between the first divisional air-feed channel 81 and the second divisional air-feed channel 82 is not limited to the valve body part 105 and the inner surface of the operation button 74, but may have a structure, for example, as illustrated in FIG. 6A. The valve device comprises a sliding surface 112 which uses an inner surface of the air-feed channel 111 as a valve seat, and a valve body 113 which slides on the sliding surface 112. The air-feed channel 111 means, for example, the first divisional air-feed channel 81 and second divisional air-feed channel 82. When the valve body 113 slides on the sliding surface 112 and moves off of the sliding surface 112, the air-feed channel 111 opens (the first divisional air-feed channel 81 and second divisional air-feed channel 82 communicate with each other). That is, the valve device opens/closes in accordance with movement of the valve body 113 relative to the sliding surface 112.

Further, the check valve 95 in the fluid control apparatus 30 as described above comprises the valve seat 96 and valve body 99, or may alternatively be configured as illustrated in FIG. 6B, for example. The check valve 95 comprises a sliding surface 112 which uses an inner surface of the air-feed channel 111 as a valve seat, and a valve body 113 which slides on the sliding surface 112. The air-feed channel 111 means, for example, the second communication channel 88 and the third communication channel 91. When the valve body 113 slides to one side on the sliding surface 112 and moves off of the sliding surface 112, the air-feed channel 111 opens. In this case, when the valve body 113 moves to another side, the valve body 113 makes contact with a stopper 114 and maintains a shut-off state in which the valve body 113 does not come off from the sliding surface 112. That is, the check valve 95 opens/closes in accordance with movement of the valve body 113 relative to the sliding surface 112.

Thus, one of the valve device (the valve body part 105 and the inner surface of the operation button 74) and the check valve 95 opens/closes in accordance with movement of the valve body 113 relative to the sliding surface 112, and shuts off, for example, communication between the first divisional air-feed channel 81 and the second divisional air-feed channel 82 as the air-feed channel or, for example, communication between the second communication channel 88 and the third communication channel 91.

Next, a gate device 120 which adjusts a leak rate of a gas leaking from the air-feed leak hole 85 will be described with reference to FIGS. 9, 10, 11, 12, and 13. Components except for the gate device 120, i.e., the endoscope 10 and fluid control apparatus 30 are the same as those described above.

As illustrated in FIG. 9, the gate device 120 comprises a gate wall 122 which slides so as to open/close the air-feed leak hole 85. The gate wall 122 adjusts an open amount of the air-feed leak hole 85.

Figure 11:
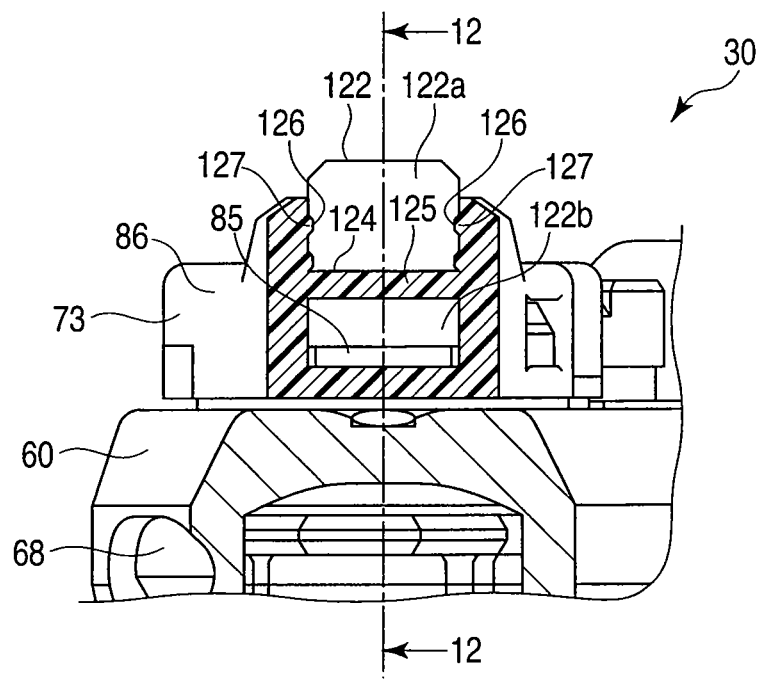
FIG. 11 illustrates the gate device.
Figure 12:
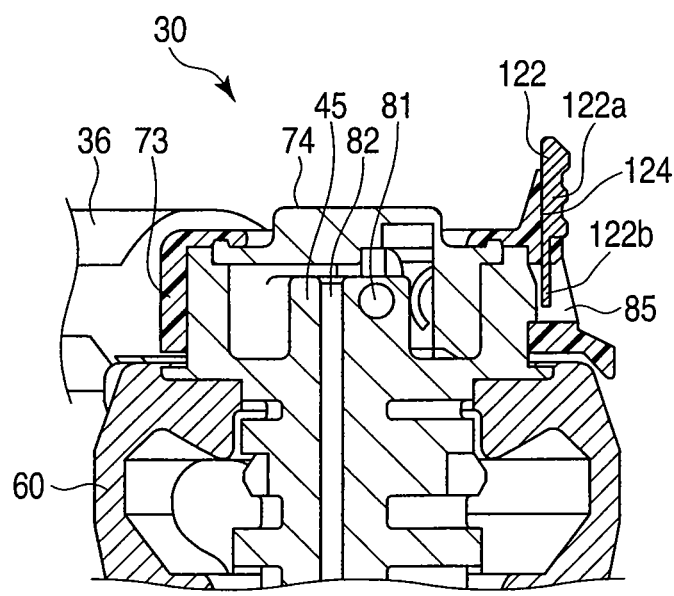
FIG. 12 is a longitudinal sectional view longitudinally cut along a center of the fluid control apparatus, to illustrate the gate device, i.e., a longitudinal sectional view longitudinally cut along a line 12-12 in FIG. 11.

The air-feed leak hole 85 is formed in a rectangle having a longer horizontal width than a vertical width, as illustrated in FIG. 11. A top edge part of a circumferential edge 125 of the air-feed leak hole 85 extends upward from a center of the finger receiver surface 86. A concave groove part 124 partitioned from the air-feed leak hole 85 is formed in the extending part. The groove part 124 is formed as a groove having a width matched with the horizontal width of the air-feed leak hole 85.

As illustrated in FIG. 13, the gate wall 122 comprises a manipulation part 122a provided in the groove part 124, and a plate-like shield part 122b which crosses the air-feed leak hole 85. The shield part 122b is provided so as to protrude from the circumferential edge 125 into the air-feed leak hole 85. Plural engagement grooves 126, which are apart from each other in sliding directions of the gate wall 122, are provided in left and right end surfaces of the manipulation section 122a. On a side wall of the groove part 124, there is provided an engagement protrusion 127 which elastically deforms relative to the engagement grooves 126 and engages in the engagement grooves 126. Further, a protruding amount by which the shield part 122b protrudes into the air-feed leak hole 85 is adjusted by selecting one of the engagement grooves 126 which is engaged with the engagement protrusion 127. Further, an opening amount (aperture) of the air-feed leak hole 85 is adjusted in accordance with the protruding amount. Further, the gate wall 122 can be detached from the groove part 124, and the fluid control apparatus 30 can be used even with the gate wall 122 positioned out of the air-feed leak hole 85. Although one of the engagement grooves 126 to engage with the engagement protrusion 127 is selected to adjust the opening amount of the air-feed leak hole 85, a method for adjusting the opening amount is not limited to this selection. The method for adjusting may employ a different moving and positioning means, such as a means of a slide type in which the engagement protrusion 127 is engaged in an engagement groove 126 by a friction force obtained by pressure using a spring. Although the gate wall 122 has been described to be movable in vertical directions of the air-feed leak hole 85, the gate wall may alternatively be movable in horizontal directions thereof.

Further, as illustrated in FIG. 10, the air-feed leak hole 85 comprising the gate wall 122 (the shield part 122b) is provided at a crossing part where an air-feed direction from the first communication channel 84 to the air-feed leak hole 85 and an air-feed direction from the air-feed leak hole 85 to the second communication channel 88 cross each other. Accordingly, air-feed flow from the first communication channel 84 to the shield part 122b is shielded by the shield part 122b, and is reversed and directed from the shield part 122b to the second communication channel 88. When the shield part 122b is provided in the air-feed leak hole 85, the opening amount of the air-feed leak hole 85 decreases and accordingly suppresses a leak rate.

Figure 14B:
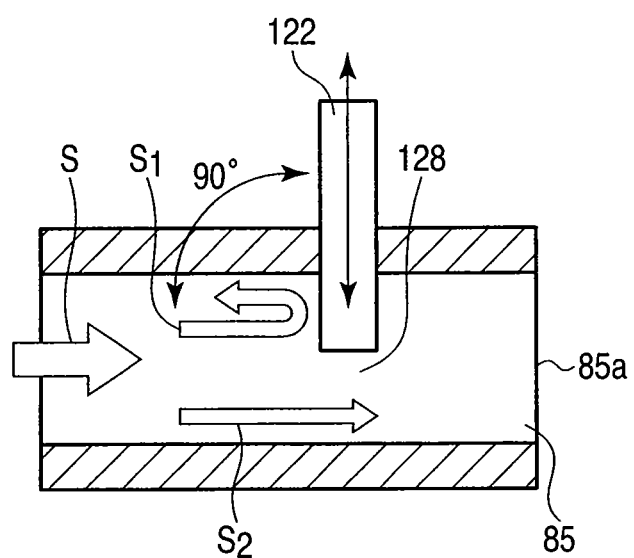
FIG. 14B illustrates an example of providing the gate wall, and a relationship between the gate wall and air-feed flow.

FIGS. 14A and 14B illustrate an example of providing the gate wall 122. FIG. 14A illustrates an example in which the gate wall 122 is arranged on an open-air surface 85a of the air-feed leak hole 85. The gate wall 122 is provided at an angle of 90° to a longitudinal sectional plane along a flow direction of air feed in the first communication channel 84. Flow S from the first communication channel 84 toward the air-feed leak hole 85 is branched into a component S1 which collides with the gate wall 122 and is reversed toward the second communication channel 88, and a component S2 which does not collide with the gate wall 122 but flows to the exterior. A slit 128 (open-air space/open-air surface 85a) has a size which varies depending on a sliding position of the gate wall 122. Therefore, the component S1 which flows to the side of the second communication channel 88, as an air-feed rate to the second communication channel 88, is adjusted. That is, the air-feed rate to the second communication channel 88 is adjusted by the size of the slit 128.

FIG. 14B illustrates an example in which the gate wall 122 is provided inside the open-air surface 85a and in the middle of the air-feed channel. The flow S from the first communication channel 84 toward the air-feed leak hole 85 is branched into the component S1 which collides with the gate wall 122 and is reversed toward the second communication channel 88, and the component S2 which does not collide with the gate wall 122 but flows to the exterior.

As described above, by adjusting the gate wall 122 in the air-feed leak hole 85, the gate device 120 changes the size of the opening of the air-feed leak hole 85, thereby adjusting the air-feed rate. For example, as the size of the opening of the air-feed leak hole 85 increases, the air-feed rate at which air leaks from the air-feed leak hole 85 increases, and accordingly, an air-feed rate at which air is fed into the second divisional air-feed channel 82 of the piston body 45 can be reduced. Further, if the size of the opening of the air-feed leak hole 85 is reduced to be small by the shield part 122b, channel resistance against air-feed flow which leaks to the exterior increases, and an air-feed rate at which air leaks from the air-feed leak hole 85 decreases. Accordingly, an air-feed rate at which air is fed into the second divisional air-feed channel 82 increases.

Further, the leak rate at the air-feed leak hole 85 can be adjusted by the gate device 120, and therefore, air can be continuously fed at a desired air-feed rate even after a finger is moved off of the air-feed leak hole 85. Accordingly, for example, when physiological narrowing of the hypopharynx, i.e., entrance of the esophagus, is observed, air needs to be constantly fed in order to expand a body cavity. In this case, a state of constantly closing the air-feed leak hole 85 with a finger needs to be maintained. Therefore, there is a risk that a user's hands are used for air-feed operation in order to feed air to the body cavity, which hinders another endoscopic operation from being conducted. However, such a risk can be avoided if the air-feed rate is adjusted by the gate device 120 as described above. Further, required air-feed rates differ between when the hypopharynx is observed and when the esophagus is observed. Such a case can also be coped with out changing a pressure of the air-feed pump. That is, when a portion with a relatively soft mucosa, such as hypopharynx, is observed closely, air feed at a relatively low flow rate is required. Alternatively, when a lumen such as an esophagus or stomach is to be instantly expanded, easier observation is available by air feed at a higher flow rate. Therefore, when the air-feed leak hole 85 is closed with a finger, air-feed operation is available at both of low and high flow rates by using the gate device 120.

Although a preferred embodiment and modifications of the present invention have been described above, the present invention is not limited to the above embodiment and modifications described above. Further, the embodiment and modifications can be variously combined with each other. Further, the above embodiment has been described about fluid transfer in air-feed and suction. However, the embodiment may be applied to air-feed, suction, and fluid transfer such as liquid-feed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic fluid control apparatus which is provided in an endoscope including a channel for performing suction and air feed and controls the suction and air feed for the channel, the apparatus comprising:

air-feed channels connected to a source of air and which communicate with the one channel;

a suction channel connected to a suction source and which communicates with the one channel;

a first valve which is provided on the air-feed channels and opens only during the air-feed;

and a second valve which is provided on an operation button to be operated for suction operation, is provided apart from one of the air-feed channels so as to maintain a space portion between the operation button and the one of the air-feed channels during the air-feed, and shuts off communication between the one of the air-feed channels and another of the air-feed channels by closing the one of the air-feed channels, which communicates with the one channel in the air-feed channels into which the operation button is inserted, when the operation button is operated to perform the suction operation, wherein the first valve is positioned in an upstream side of the space portion and the second valve in the air-feed channels;

the first valve is opened and closed independently of the second valve, the first valve is opened to feed air to the air-feed channels in a forward direction and to communicate the one of the air-feed channels to the another of the air-feed channels during the air-feed, and the first valve is closed to prevent suctioned material from flowing in a backward direction in the air feed channels and to shut off communication between the one of the air-feed channels and the another of the air-feed channels during the suction and at completion of the suction.

2. The endoscopic fluid control apparatus of claim 1, wherein at least one of the first valve and the second valve includes a valve body and a sliding surface on which the valve body slides, and a one of the first valve and the second valve opens/closes in accordance with movement of the valve body relative to the sliding surface.

3. The endoscopic fluid control apparatus of claim 2, wherein the operation button is provided in an insertion member into which the air-feed channels are inserted, the first valve is provided on the insertion member, and the second valve is provided on the insertion member through the operation button.

* * * * *